United States Patent [19]
Popescu

[11] Patent Number: 5,635,717
[45] Date of Patent: Jun. 3, 1997

[54] APPARATUS FOR DETECTING AND LOCATING RADIOACTIVE BIOLOGICAL MARKERS

[75] Inventor: Gheorghe D. Popescu, Gometz-le-Chantel, France

[73] Assignee: Dimason, Gometz-le-Chatel, France

[21] Appl. No.: 367,294
[22] PCT Filed: Jul. 16, 1993
[86] PCT No.: PCT/FR93/00729
§ 371 Date: Mar. 6, 1995
§ 102(e) Date: Mar. 6, 1995
[87] PCT Pub. No.: WO94/02868
PCT Pub. Date: Feb. 3, 1994

[30] Foreign Application Priority Data
Jul. 17, 1992 [FR] France ............................. 92 08882

[51] Int. Cl.[6] ..................... G01T 1/203; A61B 6/00
[52] U.S. Cl. ................. 250/368; 250/361 R; 250/367; 128/654; 128/659
[58] Field of Search ................. 250/361 R, 363.01, 250/370.11, 336.1, 367, 368, 369, 370.07; 128/654, 659

[56] References Cited
U.S. PATENT DOCUMENTS
4,788,436 11/1988 Koechner .................. 250/485.1
4,959,547 9/1990 Carroll et al. .................. 250/336.1

FOREIGN PATENT DOCUMENTS
0 284 542  9/1988  European Pat. Off. .
9119998  12/1991  European Pat. Off. .
2637088   3/1990  France .

OTHER PUBLICATIONS

Journal of Nuclear Medicine, vol. 29, No. 6, Jun. 1988, New York, US, pp. 1101–1106; T. S. Hickernell et al, "Dual-Detector Probe for Surgical Tumor Staging".

*Primary Examiner*—Michael J. Tokar
*Assistant Examiner*—Virgil Orlando Tyler
*Attorney, Agent, or Firm*—Nixon & Vanderhye P.C.

[57] ABSTRACT

An apparatus for sensing and locating sources of ionizing radiation retained in a turnout in a body environment, including a hand-held probe and comprising a housing with a sensor circuit for outputting a response to interaction between the radiation and the sensor; a unit for processing signals from the sensor circuit; and an indicator responding to driving signals applied thereto by generating an audible or visual output. Said hand-held probe comprises at least one scintillating plastic optical fibre (2) connecting the sensing end to a light sensor (1).

7 Claims, 1 Drawing Sheet

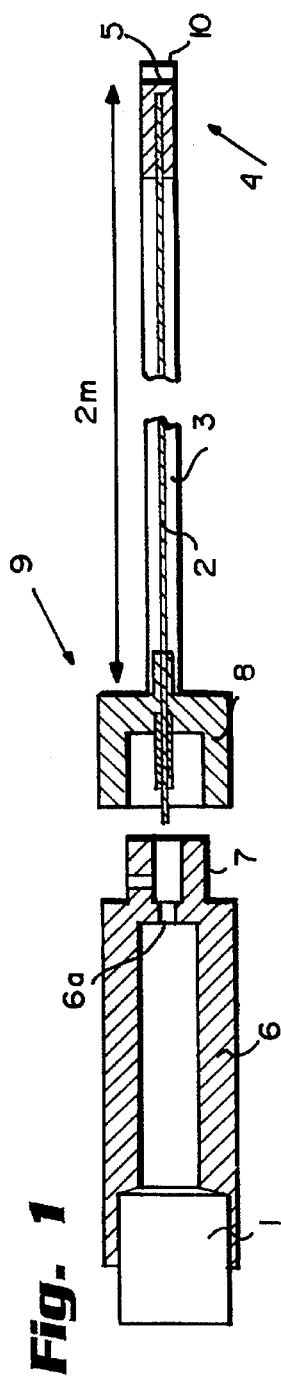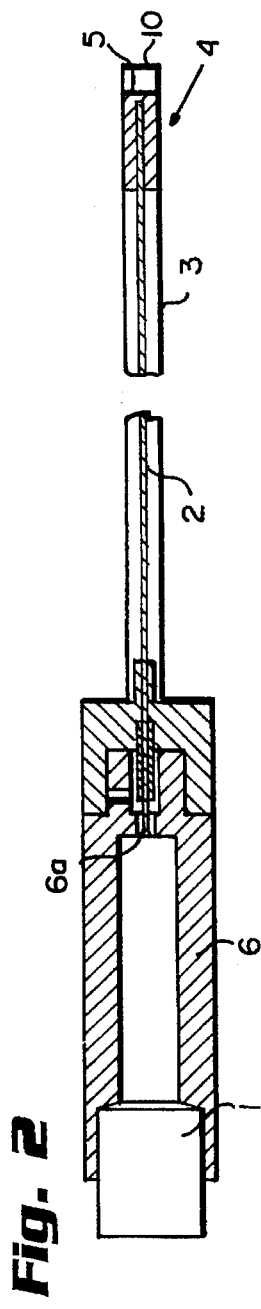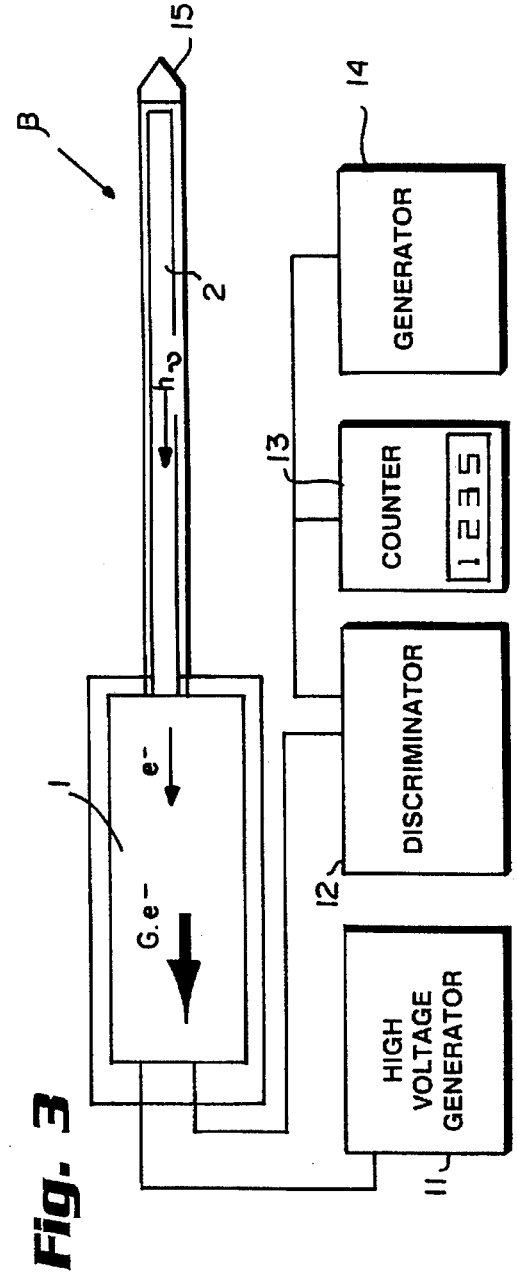

APPARATUS FOR DETECTING AND LOCATING RADIOACTIVE BIOLOGICAL MARKERS

The present invention relates to an apparatus for detecting and locating radioactive biological markers. Such an apparatus is intended for finding β and γ radiation emitted by the radioactive nuclei coupled to molecules injected into the human body before a surgical operation.

In the prior art, European Patent No. 284,542 of the company NEOPROBE CORPORATION is, in particular, known, relating to a detector and locator for the emission of low-energy radiation.

This document describes an apparatus for detecting and locating radiation sources retained by a tumor in the environment of a body exhibiting a background radiation level, comprising a probe which can be manipulated by hand and comprising a casing having an anterior portion extending to a window which can be placed in the vicinity of the source, and a portion which can be gripped by hand, extending from the anterior portion.

The apparatus of the prior art furthermore comprises a detector circuit in the casing for producing induced charges in response to an interaction of the radiation with this detector and for supplying detector signals corresponding to these charges, transmission means for transmitting these detector signals, signal processing means and warning means which respond to drive signals by emitting an output signal which is perceptible in an audible manner, in response to the drive signals which are applied to it.

The signal processing means comprise an energy-level analysis network for evaluating the detector signals with respect to the noise exhibited by the apparatus and for producing pulse data output signals representing the radiation, excluding practically all the noise, range selection means for producing a range function value for the pulse data output signals, this value representing the rate of the pulse data output signals representing the background radiation level, and control means which respond to the pulse data output signals by continuously producing the rates of appearance of these signals, over predetermined time intervals, appearing successively, the duration of which is selected in order to allow rapid updating, and responding to each discrete value of the produced rate and of the range function by producing the drive signals which have a sound-generating frequency when the value of the appearance rate is greater than the range function value, so that the audibly perceptible output signal can be varied, in response to said sound-generating frequency, while being a function of the appearance rates of the pulse data output signals lying above the background radiation level.

The active probe of such an apparatus is of considerable size, which does not allow satisfactory use in all operational cases.

An image converter associated with a bundle of scintillating optical fibers has also been proposed in the prior art (French Patent No. 2,575,858).

As in the case of the previous apparatus, the large size does not allow optimum clinical use in all operations.

The object of the present invention is to provide an apparatus for detecting and locating the β and γ radiation emitted by a radioactive tracer, which apparatus is inexpensive and is compatible with use in regions which are difficult to access.

For this purpose, the invention more particularly relates to an apparatus for detecting and locating ionizing-radiation sources retained by a tumor in the environment of a body, of the type comprising a probe which can be manipulated by hand and includes a casing comprising a detector circuit capable of producing a response to an interaction of the radiation with this detector, means for processing the signals coming from the detector circuit and warning means which respond to drive signals by emitting an audibly or visually perceptible output signal in response to the drive signals which are applied to it, characterized in that the manipulable probe comprises at least one scintillating plastic optical fiber connecting the detection end to a photodetector.

The apparatus according to the invention is composed of a casing containing all the electronic signal processing circuits, the photodetector and the power supply. This casing may be arranged at a position relatively far from the operation area, in contrast to the apparatus of the prior art which integrated at least the photodetector into the probe. The surgeon manipulates a probe which consists of the end of a flexible jacket containing the optical fiber or fibers fulfilling a first function as a light guide and a second function of converting β and γ radiation into light pulses. This jacket is very flexible and has a small diameter of a few millimeters, which allows access at locations which are inaccessible to the apparatus of the prior art.

In addition, there is no electrical connection between the casing and the part of the probe capable of coming into contact with the patient. As a result of this, the working safety of the apparatus according to the invention is reinforced in comparison to the apparatuses of the prior art, in which the photomultiplier housed in the end of the probe requires a high-voltage supply. According to an advantageous embodiment, the casing comprises a photomultiplier tube and means for optical coupling of at least one scintillating optical fiber clad in an opaque flexible jacket, the end of which constitutes said manipulable probe.

Preferably, the flexible opaque jacket is sterilizable and contains a bundle of from 2 to 6 scintillating optical fibers having a diameter of approximately 1 millimeter.

According to one advantageous embodiment, a shutter is arranged between the photomultiplier and the means for optical coupling of the bundle of scintillating fibers.

This embodiment prevents saturation of the photomultiplier when changing the probe.

According to a variant, the end of the scintillating plastic fiber is solidly attached to a functional exploration tool.

According to another variant, the end of the scintillating plastic fiber is solidly attached to a surgical tool.

According to another variant, a plurality of scintillating optical fibers, insulated from one another, form a bundle connected to a multichannel photomultiplier. This embodiment makes it possible to carry out imaging of the radioactive region. The detection ends of the fibers are organized in a matrix of N×M detection points.

The invention will be better understood on reading the following description, referring to the drawings in which:

FIG. 1 represents a sectional view of the detection part in the separated position;

FIG. 2 represents a sectional view of the detection part in the working position;

FIG. 3 represents a diagrammatic view of the apparatus according to the invention.

The detection part of the apparatus according to the invention comprises a photomultiplier (1) which converts the light signal emitted by the scintillating optical fiber (2) into an electrical signal. The photomultiplier is, for example, a photomultiplier marketed by the company PHILIPS under the reference RTC XP191, with a working diameter of 14 millimeters, having a bialkaline rubium photocathode and 10 amplification stages.

The scintillating fiber (2) is, for example, composed of a scintillator formed by a single solute dissolved in a solvent. The solute is, by way of example, 6-(4-biphenylyl) phenylbenzoxazole (PBBO). Its concentration is $4 \cdot 10^{-3}$ grams per gram of solvent, the latter being polystyrene ($n_1=1.59$). The core of the fiber is coated with a film of polymethyl methacrylate (PMMA $n_2=1.49$). The thickness of the film is approximately 3% of the diameter in the case of fibers having circular cross section, or approximately 2% of the width for fibers having square cross section. Such fibers are, in particular, marketed by the company KURABAY under the references SCS-38 or SCSF-81.

The scintillating fibers are combined into a bundle of 4 fibers (2) surrounded by a protective jacket (3) made of an opaque plastic which can be sterilized under ethylene oxide atmosphere at 55° C., for example the material marketed under the brand name ISOVERSINIC, having a thickness of one millimeter.

The front end (4) of the Bundle of fibers (2) is closed by a plug (5) made of a material identical to that forming the jacket (3). The total length of the fiber is approximately two meters.

In order to prevent dazzling the photomultiplier tube (1) when replacing the scintillating fiber, this tube is housed in a tubular part (6) whose internal surfaces are covered with an absorbent coating, for example a matt black paint. The tubular part (6) has at its end a connection adaptor (7) complementary with a plug (8) solidly attached to the end (9) of the fiber (3).

The plug (8) is housed, as represented in FIG. 2, on the adaptor (7) of the tubular part (6) in order to provide leaktight connection of the fiber (2) onto the casing. The tubular part (6) optionally includes a shutter 6a optically isolating the photomultiplier (1) from the outside light when the fiber (2) is not connected onto the adaptor (7).

FIG. 3 represents a diagrammatic view of the whole of the apparatus according to the invention.

It includes a high-voltage generator (11) delivering a photomultiplier supply voltage lying between 1000 volts and 1800 volts.

The signal coming from the photomultiplier (1) is processed by a discriminator (12) which makes a comparison with a reference voltage, adjustable between 20 and 120 millivolts, in the example described. The signal thus processed is transmitted to a counting circuit (13) and furthermore controls a sound generator (14) causing a sound signal at the detection of each pulse. This generator allows the user to find the target emitting ionizing radiation audibly, without losing view of the operation area.

The end of the scintillating fiber bundle (2) may be solidly attached to a functional exploration tool (10) as schematically shown in FIGS. 1 and 2, or to a surgical tool (15) as schematically shown in FIG. 3.

The invention is described hereinabove by way of non-limiting example. It is clear that the person skilled in the art will be capable of producing numerous variants without departing from the scope of the protection.

I claim:

1. Apparatus for detecting and locating ionizing-radiation sources retained by a tumor in the environment of a body, comprising:

a probe which can be manipulated by hand, a casing comprising a photodetector capable of producing a response to an interaction of light signals with said photodetector, a signal processor for processing electrical signals coming from said photodetector to provide drive signals, and a warning device which responds to said drive signals by emitting an audibly or visually perceptible output signal in response to said drive signals which are applied to it, wherein the manipulable probe comprises at least one scintillating optical fiber cladded with an opaque flexible jacket, and provided with a front end and a rear end, the front end being closed by a plug made of the jacket and the rear end connecting said probe to said photodetector in order to convert said light signals emitted by the scintillating optical fiber into said electrical signals.

2. Apparatus for detecting and locating radiation sources retained by a tumor according to claim 1, wherein the casing comprises a photomultiplier tube as said photodetector, housed in a tubular part and a connection adaptor at the end of said tubular part for connection of at least one scintillating optical fiber to the photomultiplier.

3. Apparatus for detecting and locating radiation sources retained by a tumor according to claim 1, wherein the flexible opaque jacket is sterilizable and contains a bundle of from 2 to 6 scintillating optical fibers having a unitary diameter of approximately 1 millimeter.

4. Apparatus for detecting and locating radiation sources retained by a tumor according to claim 2, further comprising a shutter arranged between the photomultiplier and the connection adaptor.

5. Apparatus for detecting and locating radiation sources retained by a tumor according to claim 1, wherein the front end of the scintillating plastic fiber is solidly attached to a functional exploration tool.

6. Apparatus for detecting and locating radiation sources retained by a tumor according to claim 1, wherein the front end of the scintillating plastic fiber is solidly attached to a surgical tool.

7. Apparatus for detecting and locating radiation sources retained by a tumor according to claim 2, wherein a plug solidly attached to the end of the scintillator fiber is housed in the connection adaptor of the tubular part, and wherein the tubular part is internally lined with a light-absorbent coating.

* * * * *